United States Patent [19]

Sasaki et al.

[11] 4,049,575

[45] Sept. 20, 1977

[54] PROCESS OF PRODUCING ANTIMONY-CONTAINING OXIDE CATALYSTS

[75] Inventors: Yutaka Sasaki; Akimitsu Morii, both of Yokohama; Yoshimi Nakamura, Kawasaki; Kiyoshi Moriya, Kanagawa; Hiroshi Utsumi, Yokohama, all of Japan

[73] Assignee: Nitto Chemical Industry Co., Ltd., Tokyo, Japan

[21] Appl. No.: 600,683

[22] Filed: July 31, 1975

[30] Foreign Application Priority Data

Aug. 1, 1974 Japan .................................. 49-87539

[51] Int. Cl.$^2$ ...................... B01J 21/02; B01J 27/02; B01J 27/16

[52] U.S. Cl. ................................. 252/439; 252/432; 252/435; 252/437

[58] Field of Search ................ 252/432, 435, 437, 439

[56] References Cited

U.S. PATENT DOCUMENTS 3,668,147  6/1972  Yoshino et al. .................. 252/439 X Primary Examiner—W. J. Shine Attorney, Agent, or Firm—Sughrue, Rothwell, Mion, Zinn and Macpeak

[57] ABSTRACT

A process for producing a catalyst comprising an antimony-containing oxide which comprises the steps of (A) calcining a mixture of metal oxides containing, as essential components, an oxide of antimony and an oxide of at least one metal selected from the group consisting of iron, cobalt, nickel, manganese, uranium, tin and copper, said calcining being at temperatures of from about 500° C to about 1000° C; (B) impregnating with or spraying onto said calcined mixture of metal oxides (a) an aqueous solution or a suspension containing (1) at least one compound of a metal selected from the group consisting of molybdenum, vanadium and tungsten, said metal compound being thermally convertible to an oxide of said metal, and (2) a tellurium compound, said tellurium compound being thermally convertible to a tellurium oxide, or (b) an aqueous solution or a suspension containing said metal compound (1) and an aqueous solution or a suspension containing said tellurium compound (2); (C) drying said impregnated or sprayed mixture of metal oxides and (D) calcining said dried mixture of metal oxides at a temperature of from about 400° C to about 850° C, wherein said calcining (D) is at a temperature lower than said calcining (A).

22 Claims, 5 Drawing Figures

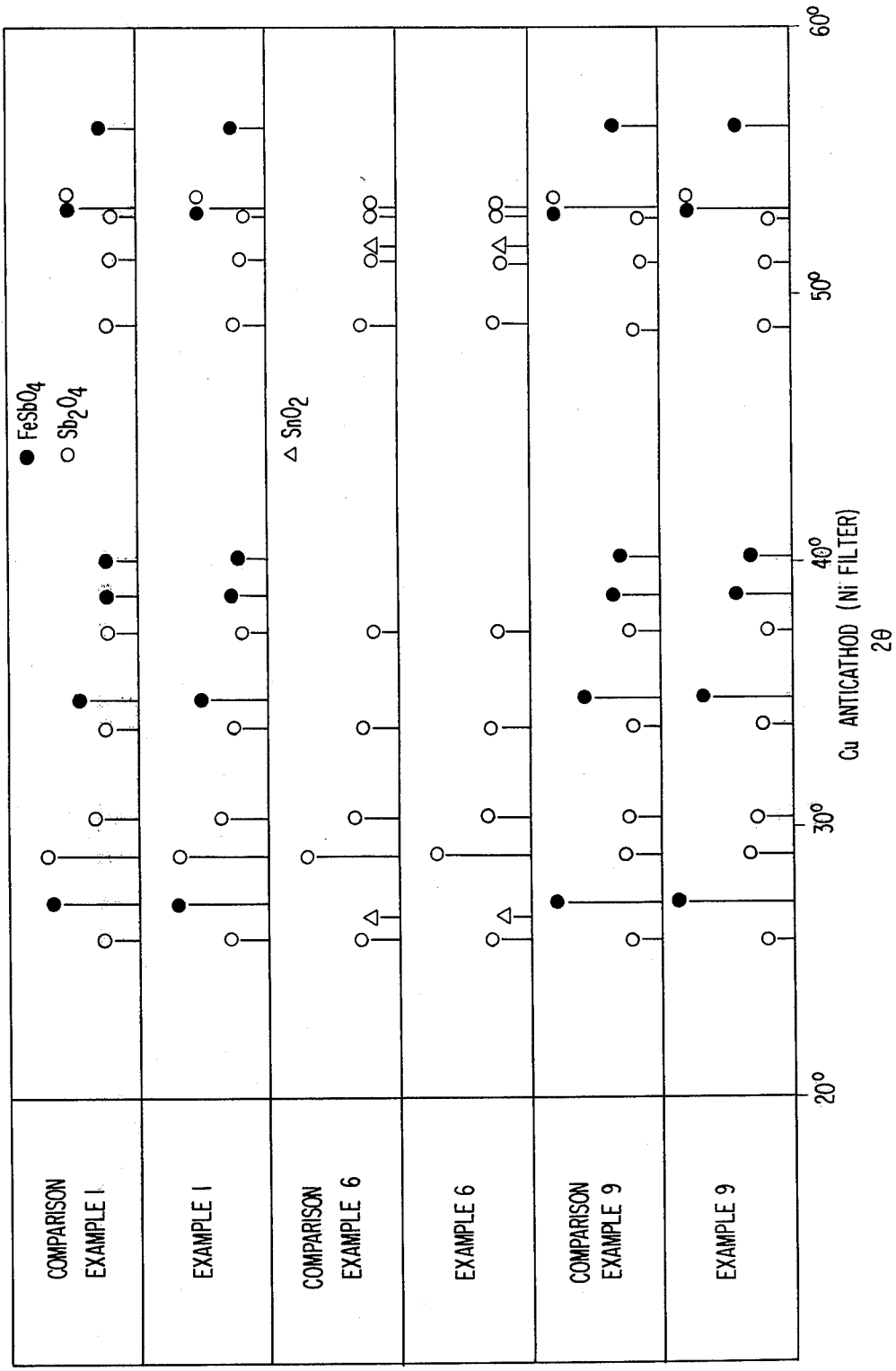

PROCESS OF PRODUCING ANTIMONY-CONTAINING OXIDE CATALYSTS

BACKGROUND OF THE INVENTION

1. Field of the Invention

The present invention relates to a process of producing an antimony-containing oxide catalyst. More specifically, the present invention relates to a process of producing an antimony-containing oxide catalyst having excellent activity which is useful for oxidation, oxidative dehydrogenation or ammoxidation of olefins.

2. Description of the Prior Art

It is well known that antimony-containing oxide catalysts, more specifically, catalysts comprising oxides of antimony and at least one metal selected from the group consisting of iron, cobalt, nickel, manganese, uranium, tin and copper are useful in the production of unsaturated aldehydes by oxidation of olefins, the production of diolefins by an oxidative dehydrogenation of olefins and the production of α-unsaturated nitriles by ammoxidation of olefins. Referring to the production of acrylonitrile by ammoxidation of propylene, for example, a catalyst comprising oxides of antimony and iron, cobalt or nickel is described in Japanese Patent Publication No. 19111/63; a catalyst comprising oxides of antimony and tin is described in U.S. Pat. No. 3,152,170; a catalyst comprising oxides of antimony and uranium is described in U.S. Pat. No. 3,198,750; and a catalyst comprising oxides of antimony and manganese or copper is described in British Pat. No. 987,960.

However, these catalysts are not satisfactory from the standpoint of the yield of the desired products obtained. Improvements have thus been made by adding certain other elemental components to these catalysts. Further, a multi-component catalyst comprising oxides of antimony and other metals which is obtained by adding an oxide of at least one metal selected from the group consisting of molybdenum, vanadium and tungsten, and tellurium to any of an oxide of antimony and iron, an oxide of antimont and tin, and an oxide or antimony and uranium, respectively, is described in U.S. Pat. No. 3,668,147 and Japanese Patent Publication Nos. 40958/72 and 19764/72. However, the greatest care must be taken in the production of a multi-component catalyst comprising antimony-other metal oxides. In order for the composition of an antimony and another metal oxide as a basic catalyst to act effectively as a catalyst in respective reactions of the oxidation of, the oxidative dehydrogenation of and the ammoxidation of olefins, first of all, it is required for each component to be bound in the form of either a solid solution or a specific oxide compound. Phrased differently, the efficiency of the catalyst is not simply determined only by the composition of active components in the catalyst but a method suitable for the production of the catalyst having the bonding as described above must be employed.

In the production of a catalyst comprising oxides, various compounds can be used as raw materials for antimony. From an industrial standpoint, howver, antimony oxides (i.e., antimony trioxide, antimony tetroxide and antimony pentoxide) or metallic antimony powder are preferably used. In using these oxides as raw materials for antimony, in order to react the antimony compounds with the polyvalent metal compounds described above the temperature employed depends on the methods for the production of the catalysts utilized. However, in general, high temperatures, e.g., 500° C to 1100° C, are required. That is, unless antimony-other metal oxide catalysts are calcined at high temperatures, the desired activity of the catalysts is not obtained.

Further, it has now been found that unless all of the additive components described above form a solid solution with the antimony-other metal oxides which are bound in a specific way as described above, the desired activity of the catalyst is not obtained in a multi-component catalyst comprising antimony-other metal oxides which is obtained by adding at least one compound of a metal selected from the group consisting of molybdenum, vanadium and tungsten and also a tellurium compound to an oxide of antimony and the polyvalent metal described hereinbefore (hereafter merely referred to as "antimony-polyvalent metal oxide").

However, some of the additive compounds in the antimony-polyvalent metal oxide catalyst give rise to differences from the antimony-polyvalent metal oxides as a basic catalyst, in the mutual reactivity thereof at high temperatures. For example, antimony-polyvalent metal oxides as a basic catalyst are difficult to sinter and require calcination at high temperatures as mentioned above. On the other hand, some of the additives described above are easily sintered and even readily vaporize. If attempts are made to form a solid solution of the additive compounds in the antimony-polyvalent metal oxides by the reaction of the antimony-polyvalent metal oxides and the additive compounds, which have these differences in properties as described above, various serious problems occur so that very severe conditions for the production of the catalysts are required. For instance, it has been found that in the case of mixing the additive compounds with the basic catalyst components in the preparation of catalysts in accordance with conventional methods, especially where a large amount of the additive compounds are added, the efficiency and physical properties of the catalysts obtained vary greatly even with slight changes in calcination temperatures and therefore, it is extremely difficult to consistently produce catalysts having the desired activity and physical properties.

SUMMARY OF THE INVENTION

The present invention has solved these problems, i.e., provides a process for easily producing a multi-component oxide catalyst comprising an antimony-polyvalent metal oxide which is less dependent on the calcination temperature and which has excellent activity and physical properties, by either impregnating with or spraying on the basic calcined oxide catalyst, the additive components, and calcining the catalyst generally at lower temperatures than the calcination temperatures of the basic oxide catalyst.

Accordingly, this invention provides a process for producing an antimony-containing oxide catalyst comprising the steps of calcining a metal oxide mixture composition containing, as essential components, an oxide of antimony and an oxide of at least one metal selected from the group consisting of iron, cobalt, nickel, manganese, uranium, tin and copper at a temperature of from about 500° C to about 1000° C, impregnating with or spraying on the calcined metal oxide mixture composition an aqueous solution or a suspension containing (1) at least one metal compound of a metal selected from the group consisting of molybdenum, vanadium and tungsten, and (2) a tellurium compound; drying the thus formed metal oxide mixture composition; and then calcining the metal oxide mixture composition at a temperature of from about 400° C to about 850° C.

In another embodiment of this invention, the invention provides a process for producing an antimony-containing oxide catalyst comprising the steps of calcining a metal oxide mixture composition, containing as essential components, an oxide of antimony and an oxide of at least one metal selected from the group consisting of iron, cobalt, nickel, manganese, uranium, tin, and copper at a temperature of from about 500° C to about 1000° C, impregnating with or spraying on the calcined metal oxide mixture composition an aqueous solution or a suspension containing (1) at least one metal compound of a metal selected from the group consisting of molybdenum, vanadium and tungsten, (2) a tellurium compound, and (3) at least one compound of a metal selected from the group consisting of iron, cobalt, nickel, manganese, copper, zinc, potassium, magnesium, aluminum, zirconium, bismuth, lanthanum, cerium, chromium, phosphorus and boron; drying the thus formed metal oxide mixture composition; and calcining the metal oxide mixture composition at a temperature of from about 400° C to about 850° C.

BRIEF DESCRIPTION OF THE DRAWINGS

FIG. 5 is an X-ray diffraction pattern of each catalyst of Comparison Example 1, Example 1, Comparison Example 6, Example 6, Comparison Example 9 and Example 9.

DETAILED DESCRIPTION OF THE INVENTION

As described above, the process of producing an antimony-containing oxide catalyst according to the present invention comprises the steps of calcining a metal oxide mixture composition containing, as essential components, an oxide of antimony and an oxide of at least one metal selected from the group consisting of iron, cobalt, nickel, manganese, uranium, tin and copper at temperatures of from about 500° C to about 1000° C, impregnating with or spraying on the calcined metal oxide mixture composition an aqueous solution or a suspension containing (1) at least one metal compound of a metal selected from the group consisting of molybdenum, vanadium and tungsten and (2) a tellurium compound, drying the thus formed metal oxide mixture composition, and calcination of the metal oxide mixture composition at temperatures of from about 400° C to about 850° C, preferably 400° C to 750° C.

In one embodiment of the present invention, the calcined oxide mixture composition can further be impregnated or sprayed with an aqueous solution or a suspension containing (1) at least one metal compound of a metal selected from group consisting of molybdenum, vanadium and tungsten and (2) a tellurium compound, and further containing (3) at least one compound of a metal selected from the group consisting of iron, cobalt, nickel, manganese, copper, zinc, potassium, magnesium, aluminum, zirconium, bismuth, lanthanum, cerium, chromium, phosphorus and boron.

A most advantageous characteristic in the practice of the present invention is that a catalyst having excellent activity and physical properties can be easily produced in a stable manner because a catalyst less dependent on the calcination temperature can be obtained.

Figure 1:
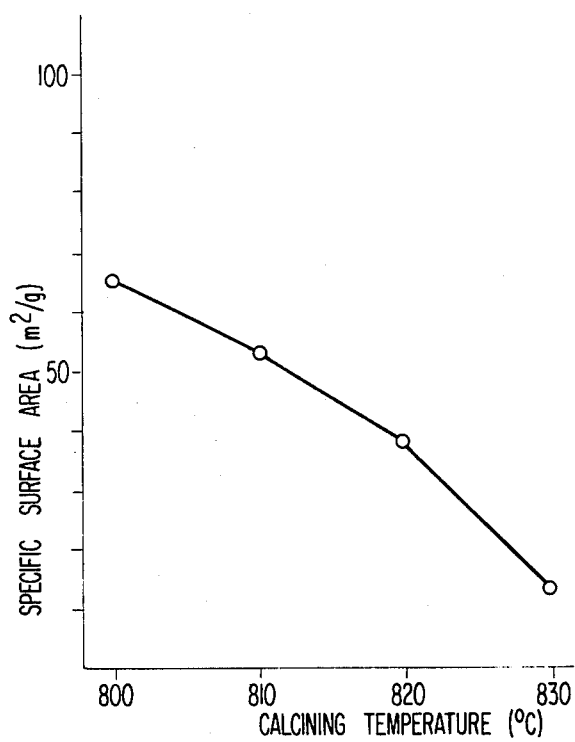
FIG. 1 and FIG. 2 show the dependency of the specific surface area on calcination temperatures and the dependency of the results of the reaction (i.e., the yield of acrylonitrile) on the calcination temperatures around the optimum calcination temperature of the catalyst of Comparison Example 8-3, respectively.
Figure 2:
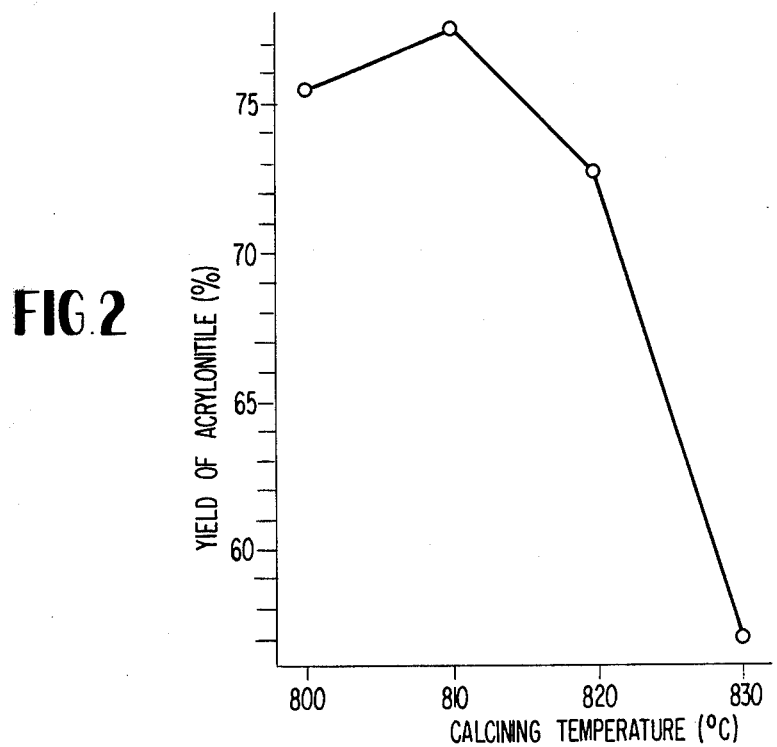

For example, with regard to the catalyst of Comparison Example 8 obtained as described hereinafter, which was prepared by initially mixing all of the catalyst components as raw materials, the relationship between the calcination temperatures and specific surface area of the catalyst around the optimum calcination temperature of the catalyst is shown in FIG. 1, whereby only the calcination temperatures of the catalyst are varied; and when the catalyst is used in the ammoxidation of propylene (the reaction conditions are the same as described in Table 1 hereinafter), the relationship between the calcination temperatures of the catalyst and the catalyst activity, i.e., the yield of acrylonitrile (as defined hereinafter) is shown in FIG. 2, respectively. As can be seen from the results in FIG. 1 and FIG. 2, only a slight change in calcination temperatures of from 800° C to 830° C results in a marked decrease in the specific surface area of from 65 m²/g to 13 m²/g and a decrease in the yield of acrylonitrile of from 77% to 57%. It is thus evident that the activity of the catalyst is greatly dependent on the calcination temperatures employed.

Figure 3:
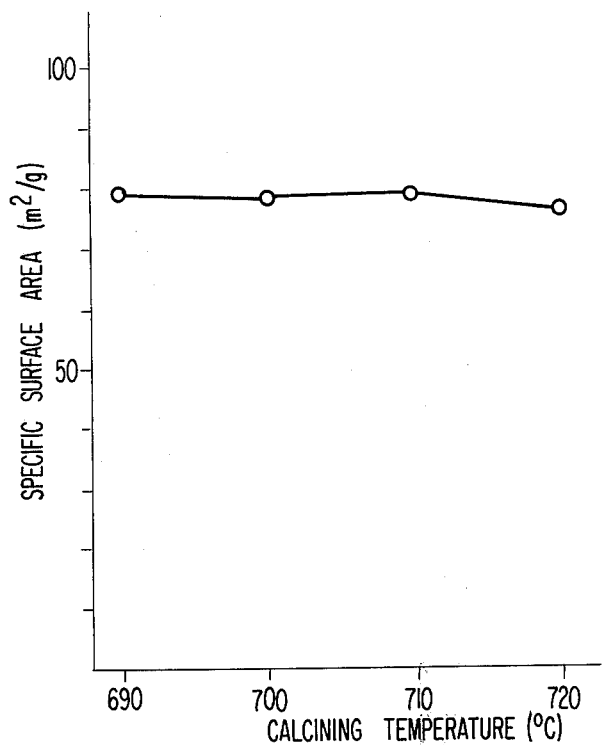
FIG. 3 and FIG. 4, respectively, show the dependency of the specific surface area on calcination temperatures and the dependency of the results of the reaction (i.e., the yield of acrylonitrile) on the calcination temperatures around the optimum calcination temperature of the catalyst of Example 8-5.
Figure 4:
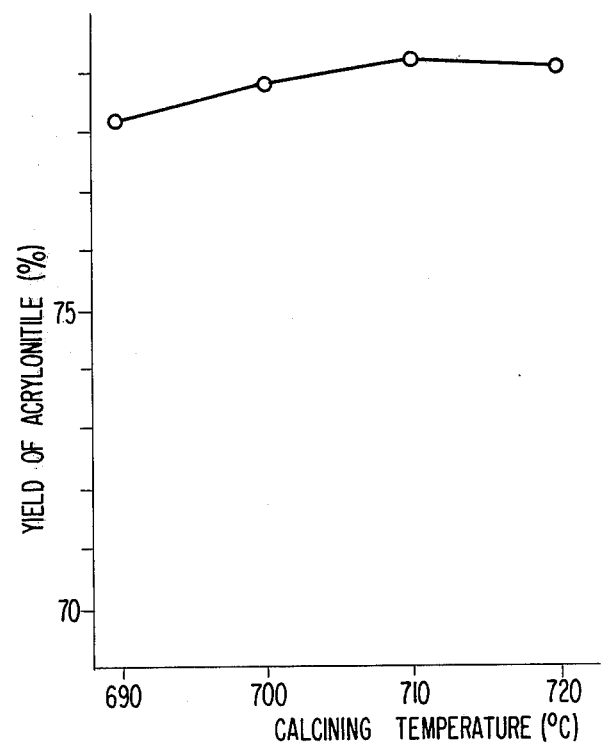

On the other hand, with regard to the catalyst of Example 8-5 obtained as described hereinafter, which was prepared by spraying the additive components, i.e., the molybdenum, vanadium and/or tungsten component and the tellurium component onto the calcined basic catalyst in accordance with the present invention, the relationship between the calcination temperatures and the specific surface area of the catalyst around the optimum calcination temperature of the catalyst is shown in FIG. 3, whereby only the calcination temperatures of the sprayed catalyst are varied; and when the catalyst is used in the ammoxidation of propylene (the reaction conditions are the same as described in Table 1 hereinafter), the relationship between the calcination temperatures of the catalyst and the catalyst activity, i.e., the yield of acrylonitrile (as defined hereinafter) is shown in FIG. 4, respectively. As can be seen from the results in FIG. 3 and FIG. 4, even if the calcination temperatures change from 690° C to 720° C, the specific surface area as well as the yield of acrylonitrile do not substantially change, i.e., the dependency of the activity of the catalyst on the calcination temperatures is extremely low. Such a low dependency of the catalyst activity and the physical properties of the catalyst on calcination temperature is extremely advantageous in the production of catalysts on an industrial scale since the temperature in the calcination of the catalyst can easily be controlled.

It can also be seen from a comparison of the results in FIG. 2 with those in FIG. 4 that the catalyst obtained in accordance with the present invention provides a superior yield of the desired product (acrylonitrile in this instance) to the yield in using the catalyst obtained in accordance with a conventional method. That is, it can be seen that by adopting the process of the present invention, the additive components described above effectively react with the components of the basic catalyst to improve the efficiency of the catalyst.

While the composition of the catalyst which is prepared in accordance with the present invention is not critical, a preferred composition of the catalyst falls within the following empirical formula:

$$Me_a Sb_b X_c Te_d R_e O_f$$

in which Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts $a$, $b$, $c$, $d$, $e$ and $f$ each respresents the atomic ratios of the components to which they refer in which: when $a$ is 10;
- $b$ = about 5 – 60;
- $c$ = about 0.05 – 30, preferably 0.1 – 15;
- $d$ = about 0.05 – 10, preferably 0.1 – 5;
- $e$ about 0 – 20; preferably 0 –10; and
- $f$ = the number of oxygens corresponding to the oxides formed by each of the components described above and generally ranges from about 25 to 215, preferably 25.5 to 180.

The catalyst which is prepared in accordance with the present invention can be employed without any carrier but, if desired, the catalyst can be employed supported on an appropriate carrier. Many known carriers can be employed in the present invention. Specific examples of suitable carriers include silica, alumina, titania, zirconia, silica-alumina, etc. Silica is the most preferred of these carriers. The amount of the carriers to be used should be determined by physical properties or reaction rates of the catalyst required but, in general, preferably about 10 to about 90% by weight to the total weight of the catalyst is suitable.

In the process of the present invention, the antimony-polyvalent metal oxide composition is initially calcined at temperatures of from about 500° C to about 1000° C. The calcination can be carried out at a single temperature or using a combination of a preliminary calcination and a calcination at high temperatures. If calcination at high temperatures, e.g., above 700° C, is desired, the combination of a preliminary calcination plus a calcination at high temperatures is preferred. In this case, the preliminary calcination is preferably carried out at about 200° C to about 600° C. The optimum calcination conditions will vary depending upon the composition of the catalyst, but generally, the preliminary calcination is preferably carried out at about 200° C to about 600° C for about 1 to about 50 hrs., followed by calcination at high temperatures of from about 600° C to about 1000° C. for about 1 to about 50 hrs.

The antimony-polyvalent metal oxide composition which is a basic catalyst can also contain a small amount of molybdenum, vanadium, tungsten, tellurium, zinc, potassium, magnesium, aluminum, zirconium, bismuth, lanthanum, cerium, chromium, phosphorus, boron, etc.

The thus-calcined antimony-polyvalent metal oxide composition is then impregnated with an aqueous solution or suspension containing (1) at least one compound of a metal selected from the group consisting of molybdenum, vanadium and tungsten and (2) a tellurium compound or the aqueous solution or suspension as described above is sprayed onto the antimony-polyvalent metal oxide composition.

The starting material for the antimony component can be an antimony oxide such as, for example, antimony trioxide, antimony tetroxide or antimony pentoxide. Also, those compounds which are finally stabilized as antimony oxide after chemical treatment, calcining treatment or the like can be used. For example, these compounds include hydrous antimony oxide, metaantimonic acid, orthoantimonic acid, pyroantimonic acid or the like. Metallic antimony oxidized with nitric acid can also be used. Also, hydrolyzable antimony salts such as antimony halides, for example, antimony trichloride and antimony pentachloride can be used. These antimony halides are hydrolyzed with water into hydrous oxides.

The starting material for providing the iron component of the catalyst can be selected from many materials. For example, iron oxide in the form of ferrous oxide, ferric oxide or ferroferric oxides can be used. Also, compounds which are finally stabilized as iron oxide after chemical treatment, calcining treatment or the like can be used. Those compounds include iron salts of inorganic acids such as iron nitrate and iron chloride, iron salts of organic acids such as iron acetate and iron oxalate, etc. The salts can be converted into oxides by neutralizing them with a basic substance such as aqueous ammonia to form iron hydroxide and then calcining the iron hydroxide or by directly calcining these salts. Further, iron hydroxide or metallic iron can be used. The metallic iron can be added in the form of a fine powder or can be treated with hot nitric acid. In the latter case, iron is converted into ferric nitrate. Whatever starting material is selected, it is important to intimately mix the material with other components. Therefore, the material is preferably added in the form of fine powder, aqueous solution or sol.

As starting materials for the cobalt, nickel, chromium, copper, manganese, bismuth, and cerium components, nitrates thereof, which are soluble in water and capable of providing nitrate ion, can conveniently be used. As starting materials for the vanadium component, water-soluble compounds such as ammonium metavanadate and vanadyl oxalate can conveniently be used. As starting materials for the molybdenum and tungsten components, water-soluble compounds such as ammonium para(or meta)molybate and ammonium para(or meta)-tungstate can conveniently be used. As starting materials for the titanium component, chlorides thereof can preferably be used, since they are partially water-soluble in an aqueous medium containing hydrochloric acid and can provide finely divided oxychlorides and oxide particles upon hydrolysis in the medium. As starting materials for the tellurium component, any of the acids and oxides thereof can be used, such as, for example, telluric acid, tellurous acid, tellurium dioxide, the tellurium dioxide being used in the form of a solution comprising nitric acid which serves as an oxidizing agent and tellurium.

The starting material for the phosphorus or boron component can be any phosphorus or boron compound, but it is most convenient to add the component in the form of phosphoric acid or boric acid.

The starting material for the tin component can be selected from many materials. For example, stannous oxide and stannic oxide can be used. Also, compounds which are finally stabilized as tin oxide after chemical treatment, calcining treatment or the like can be used. For example, tin halides such as stannous chloride and stannic chloride can be used upon hydrolysis. Further, metallic tin can also be used. In this case, the metallic tin can be used by oxidation with nitric acid. Whatever starting material is selected, it is important to intimately mix the starting material with other components.

The starting material for the uranium component can also be selected from many materials. For example, uranium dioxide ($UO_2$), uranium trioxide ($UO_3$) or the like can be used. Also, compounds which are finally stabilized as uranium oxide after chemical treatment, calcining treatment or the like can be used. These compounds include an inorganic or organic salt or oxy salt such as uranyl nitrate ($UO_2(NO_3)_2.6H_2O$), uranium hexafluoride ($UO_3$), uranyl acetate ($UO_2(CH_3COO)_2.2H_2O$) and the like. The salts can be converted into oxides by neutralizing the salts with a basic substance such as aqueous ammonia and then calcining, or by directly calcining the salts to form oxides. Further, metallic uranium can be used. In this case, metallic uranium dissolved in nitric acid can be used. Whatever the starting material is selected, it is important to intimately mix the starting material with other components.

Preferred examples of molybdenum compounds are molybdenum trioxide, molybdic acid, ammonium paramolybdate, ammonium metamolybdate, etc. Of these molybdenum compounds, ammonium paramolybdate is particularly preferred.

Preferred examples of vanadium compounds are vanadium pentoxide, ammonium metavanadate, vanadyl oxalate, etc. Particularly, ammonium metavanadate and vanadyl oxalate are preferred.

Preferred examples of tungsten compounds include tungsten trioxide, tungstic acid, ammonium paratungstate, etc., of which ammonium paratungstate is particularly preferred.

Preferred examples of tellurium compounds include those in which metallic tellurium, tellurium dioxide, tellurous acid, etc., are dissolved in nitric acid, telluric acid, etc.

In order to impregnate the calcined oxide composition with or spray thereonto the additive compounds, impregnation or spraying the composition with a solution or suspension containing all of the additive compounds to be employed is convenient. Where it is difficult to prepare a solution or suspension containing all of the additive compounds to be employed at a definite concentration, the calcined oxide composition can be individually impregnated with or sprayed with solutions or suspensions each containing one of the components. The method employed for impregnation or spraying is optional.

Various methods for impregnation can be employed, for example, the following methods are suitable.

The pore volume of the catalyst to be impregnated is previously measured. An impregnating solution or suspension having a concentration corresponding to the pore volume of the catalyst is prepared. Then, the catalyst is impregnated with the solution or suspension and sufficient time is allowed for the solution or suspension to penetrate into the pores. In general, about 20 mins. to 2hrs. is sufficient. Thereafter, the catalyst is separated from the impregnating solution or suspension, dried and calcined to obtain the final catalyst.

Instead of impregnating the catalyst with the impregnating solution or suspension, the solution or suspension is weighed so as to correspond to the pore volume and thoroughly mixed with the catalyst. In the case of a particulate catalyst, e.g., for a fluidized bed, this method is particularly suitable.

In addition the impregnating solution or suspension can be sprayed on the catalyst. For example, the impregnating solution or suspension can be sprayed onto the catalyst while rotating the catalyst in a rotating drum. However, since the amount carried onto the catalyst tends to vary in every particle of the catalyst, care must be taken in handling.

The additive components described above to be added to the basic catalyst, i.e., the calcined antimony-polyvalent metal oxide composition, by impregnation or spraying are effective in an amount of less than about 10% by weight, calculated as the oxides thereof, based on the basic catalyst weight, i.e., the weight of the basic catalyst containing antimony and the iron, cobalt, nickel, manganese, uranium, tin and/or copper after the initial calcination. In most cases, an amount of less than 5% by weight is sufficient. A preferred ratio of the additive components described above is, as an atomic ratio:

(Mo/V/W) : Te = 1: 0.1 to 5.0

After impregnating the basic catalyst with or spraying thereon the additive components described above, the thus formed oxide composition is dried, e.g., at about 50° to 300° C, preferably 100° to 200° C, and finally calcined at temperatures of about 400° C to about 850° C. The optimum calcination conditions will vary depending upon the kind and amount of the aditive components. However, since the influence of the calcination conditions on the activity and the physical properties of the catalyst is not very serious, the production of the catalyst is easily controlled and, in general, calcination at temperatures of about 400° C to about 850° C for about 1 to about 50 hrs. is preferred. If calcination at high temperatures is desired, a preliminary calcination is preferably carried out at temperatures of about 200° C to about 600° C, as in the calcination prior to the impregnation or spraying.

While the manner in which the components added by impregnation or spraying are bound with the components of the basic catalyst is not completely understood, it has been found that each component of molybdenum, vanadium, tungsten and tellurium is dissolved as a solid solution thereof in the crystal structure of the basic catalyst in the calcination of the catalyst. Further, it has been found that these additive components synergestically and mutually accelerate the formation of a solid solution.

The effects obtained by the addition of a molybdenum, vanadium, tungsten and tellurium component are described in U.S. Pat. No. 3,668,147, and Japanese Patent Publication Nos. 19764/72 and 40958/72. That is, a catalyst comprising antimony-polyvalent metal oxides tends to be reduced and tends to lose its catalytic activity under a reductive atmosphere. Accordingly, the catalyst has the defects that if oxidation, oxidative dehydrogenation or ammoxidation of olefins is attempted using the catalyst either by increasing the concentration of the olefins or by decreasing the partial pressure of the oxygen, a decrease in the selectivity for the desired product would result, and in the extreme case, a permanent change or deterioration of the catalyst would result. By the addition of at least one component selected from the group consisting of molybdenum, vanadium and tungsten, the activity of the catalyst can be maintained even at low oxygen partial pressures. By the further addition of the tellurium component, the selectivity for the desired product can be improved without deteriorating the activity of the catalyst at low oxygen partial pressures.

In the impregnation of or spraying on the calcined antimony-polyvalent metal oxide composition, in addition to an aqueous solution or suspension containing at least one compound of a metal selected from the group consisting of molybdenum, vanadium and tungsten, and a tellurium compound, the calcined oxide composition as described in the second embodiment above can further be impregnated or sprayed with an aqueous solution or a suspension containing at least one compound of a metal selected from the group consisting of iron, cobalt, nickel, manganese, copper, zinc, potassium, magnesium, aluminum, zirconium, bismuth, lanthanum, cerium, chromium, phosphorus and boron, as a supplemental additive component(s) and the effects of the present invention are thus further improved. That is, the impregnation with or spraying of one or more of the supplemental additive compounds described above results in the effect of stabilizing the bonding of each of the molybdenum, vanadium, tungsten and tellurium components with the basic catalyst and in some cases, the yield of the product obtained somewhat increases.

The following materials can be employed as starting materials for these supplemental additive components.

Specific examples of iron compounds which can be used include iron powders dissolved in nitric acid, iron nitrate, iron chloride, iron acetate, iron hydroxide, etc.

Specific examples of copper compounds which can be used include metallic copper or copper oxides dissolved in nitric acid, copper nitrate, copper chloride, etc.

Specific examples of magnesium compounds which can be used include magnesium nitrate, magnesium oxide, etc.

Specific examples of zirconium compounds which can be used include zirconium oxynitrate, zirconium hydroxide, etc.

Preferred examples of zinc, bismuth, lanthanum, cerium, aluminum, chromium, manganese, cobalt, nickel and potassium compounds are the nitrates, chlorides, hydroxides, etc., thereof.

Impregnation with or spraying of the calcined oxide composition with the supplemental additive compounds can be conveniently carried out by impregnating or spraying with a solution or suspension obtained by mixing at least one compound of a metal selected from the group consisting of molybdenum, vanadium and tungsten and a tellurium compound and also adding one or more of the supplemental additive compounds described above. Individual solutions or suspensions containing the respective components can also be employed independently for impregnation or spraying. Suitable methods can be employed depending upon the objects.

A sufficient total amount of the above-described additive components and supplemental additive components to be added to the basic catalyst, i.e., the calcined antimony-polyvalent metal oxide composition, is below about 10% by weight, calculated as the oxides, to the weight of the basic catalyst, i.e., the weight of the basic catalyst containing antimony and the iron, cobalt, nickel, manganese, uranium, tin and/or copper after the initial calcination, and in most cases, is below 5% by weight. A preferred ratio of the above described additive and supplemental additive components is, as an atomic ratio:

(Mo/V/W) : Te : (Fe/Co/Ni/Mn/Cu/Zn/K/Mg/Al/Zr/Bi/La/Ce/Cr/ P/B) = 1 : 0.1 – 5.0 : 0.1 – 5.0

Where the compounds containing the same components as those already contained in the basic catalyst composition are employed as supplemental additive components, the components can not be distinguished in the composition from those previously present in the basic catalyst. However, it is assumed from experimental results obtained that the components added later have a greater influence on the activity of the catalyst than those previously present in the basic catalyst. More specifically, when the amount of the polyvalent metal oxides employed is somewhat decreased and the basic catalyst is impregnated or sprayed with the same polyvalent metal compounds in an amount corresponding to the decreased amount, the efficiency of the catalyst is further improved as compared with the case where the total amount of the polyvalent metal compounds is initially present prior to the calcination to produce the antimony-polyvalent metal oxide basic catalyst.

In the catalyst which is obtained in accordance with the present invention, the additive components and supplemental additive components are not present in a free oxide state. This has been proved by the X-ray diffraction pattern obtained. For example, the X-ray diffraction patterns of the catalyst obtained in Examples 1, 6 and 9 and Comparison Examples 1, 6 and 9 described hereinafter are shown in FIG. 5, respectively. Comparing the catalysts of Comparison Example 1 with Example 1, Comparison Example 6 with Example 6 and Comparison Example 9 with Example 9, the same X-ray diffraction patterns are obtained in each of the corresponding examples as in the comparison examples. It is thus evident that no oxides of only the components added later are observed. If the components added are present as free oxides, the activity of the catalyst is decreased.

The present invention can be employed when conventional multi-component catalysts comprising antimony-polyvalent metal oxides having inferior efficiency are modified to improve the efficiency thereof. In addition, the present invention can also be employed for reactivation of multi-component catalysts comprising antimony-polyvalent metal oxides, whose activity has deteriorated, due to some reason, by change due to reduction, or by loss of the additive components during the use thereof.

A modification of the present invention is characterized in that in a catalyst comprising antimony-containing oxides, after the catalyst in which the activity has been deteriorated by change due to reduction, or by a loss of the above described additive compounds is impregnated or sprayed with an aqueous solution or a suspension containing (1) at least one compound of a metal selected from the group consisting of molybdenum, vanadium and tungsten and (2) a tellurium compound, the thus formed metal oxide mixture composition is dried and calcined at temperatures of about 400° C to about 850° C.

In another modification of the present invention, the catalyst in which the activity has been deteriorated by change due to reduction, or by a loss of the additive compounds, can be impregnated or sprayed with an aqueous solution or suspension obtained by mixing an aqueous solution or a suspension containing (1) at least one compound of a metal selected from the group consisting of molybdenum, vanadium and tungsten (2) a tellurium compound and (3) at least one compound of a metal selected from the group consisting of iron, cobalt, nickel, manganese, copper, zinc, potassium, magnesium, aluminum, zirconium, bismuth, lanthanum, cerium, chromium, phosphorus and boron.

In these modifications the intitial calcination step in the standard method is omitted but the step of impregnation or spraying, the step of drying of the formed oxide composition followed by calcination are performed in the same manner as in the basic method described hereinbefore. In these modifications, the additive compound is already contained at least partly prior to the step of impregnation or spraying. However, it is sufficient to impregnate or spray with the additive compounds in a ratio of the additive components which is the same as in the basic method.

The process of producing a catalyst in accordance with the present invention can provide in a stable manner and easily a multi-component catalyst comprising an antimony-polyvalent metal oxide which has excellent activity and physical properties and in addition, can effectively be utilized in the improvement and activation of oxide catalysts of inferior efficiency. Further, the process of the present invention is advantageous from an economical standpoint because the catalyst components to be added by impregnation or spraying effectively act on the efficiency of the catalyst and consequently, exhibit effects equivalent to or more than that in the case of adding such components previously, since expensive catalyst components are employed.

The features of the present invention and the results obtained thereby will be explained in great detail with reference to the following Examples and Comparison Examples. Unless otherwise indicated herein, all parts, percentages, ratios and the like are by weight.

The yield and selectivity of the product obtained referred to in the present specification were obtained by the following relationships:

$$\text{Yield (\%)} = \frac{\text{Weight of carbon in the product obtained}}{\text{Weight of carbon in starting material hydrocarbon supplied}} \times 100$$

$$\text{Selectivity (\%)} = \frac{\text{Weight of carbon in the product obtained}}{\text{Weight of carbon in starting material hydrocarbon reacted}} \times 100$$

Evaluation of the activity of the catalyst was carried out as follows

Evaluation of Catalyst Activity

1. Ammoxidation of Propylene

Test Condition 1:

In a U-shaped fixed bed type reactor of an inner diameter of 16 mm and a length of 500 mm, 2.5 ml of a catalyst molded into a cylindrical shape of 2 mm × 2 mmα was filled. The system was heated in a molten salt bath of a mixture of sodium nitrite and potassium nitrate in an equivalent amount to maintain a fixed reaction temperature. Into the reactor, a gas having the following composition was fed at a rate of 10 l (STP)/hr. The reaction pressure used was normal pressure.

$O_2$ (fed as air)/Propylene = 2.1 (molar ratio)
$NH_3$/Propylene = 1.2 (molar ratio)

Test condition 2:

In a fluidized bed type reactor, in which the inner diameter was 2 inches and the length was 2 m, a catalyst was filled in a suitably selected amount within the range of 1200 g to 1800 g. Into the reactor, a gas having the following composition was fed at an apparent linear velocity of 15 cm/sec. The reaction pressure used was normal pressure.

$O_2$ (fed as air) / Propylene = 2.10 (molar ratio)
$NH_3$ / Propylene = 1.15 (molar ratio)

2. Ammoxidation of Isobutene

Test Condition 3:

In a U-shaped fixed bed reactor of an inner diameter of 16 mm and a length of 500 mm, 20 ml of a catalyst molded into a cylindrical shape of 2 mm × 2 mm$\phi$ was filled. The system was heated in a molten salt bath of a mixture of sodium nitrite and potassium nitrate in an equivalent amount to maintain a definite reaction temperature. In the reactor, a gas having the following composition was fed at a rate of 10 liters (STP)/hr. The reaction pressure used was normal pressure.

$O_2$ (fed as air) / Isobutene = 3.5 (molar ratio)
$NH_3$ / Isobutene = 1.3 (molar ratio)

3. Oxidative Dehydrogenation of Butene-1

Test Condition 4:

In a U-shaped fixed bed reator of an inner diameter of 16 mm and a length of 500 mm, 25 ml of a catalyst molded into a cylindrical shape of 2 mm × 2 mm$\phi$ was filled. The system was heated in a molten salt bath of a mixture of sodium nitrite and potassium nitrate in an equivalent amount to maintain a definite reaction temperature. In the reactor, a gas having the following composition was fed at a rate of 7.5 l liters (STP)/hr. The reaction pressure used was normal pressure.

$O_2$ (fed as air) / Butene-1 = 1.1 (molar ratio)
Water / Butene-1 = 1.5 (molar ratio)

4. Oxidation of Propylene

Test Condition 5:

In a U-shaped fixed bed reactor of an inner diameter of 6 mm and length of 500 mm, 25 ml of a catalyst molded into a cylindrical shape of 2 mm × 2 mm$\phi$ was filled. The system was heated in a molten salt bath of a mixture of sodium nitrite and potassium nitrate in an equivalent amount to maintain a definite reaction temperature. In the reactor, a gas having the following composition was fed at a rate of 12 liters (STP)/hr. The reaction pressure used was normal pressure.

$O_2$ (fed as air) / Propylene = 2.2 (molar ratio)
Water / Propylene = 4.0 (molar ratio)

Preparation of Catalyst and Activity Evaluation Thereof

Example 1 and Comparison Example 1

A catalyst having the empirical formula of $Fe_{10}Sb_{60}O_{135}\cdot(SiO_2)_{60}$ was prepared as follows.

To 270 ml of heated nitric acid (specific gravity: 1.38) was gradually added 73.3 g of metallic antimony powder (below 100 mesh). After the addition of the antimony was completed and the evolution of a brown gas ceased, the mixture was allowed to stand at room temperature for 16 hrs. Thereafter, the excess nitric acid was removed and the precipitate was washed with water five times (1). Electrolytic iron powder (5.6 g) was gradually added to a liquid mixture of 41 ml of nitric acid (specific gravity: 1.38) and 50 ml of water to completely dissolve the iron (II).

180 g of a silica sol ($SiO_2$: 20% by weight) was used as a carrier component (III).

The three components above (I), (II) and (III), were mixed. Aqueous ammonia (28%) was added incrementally to the mixture while agitating the mixture to adjust the pH to 2. The resulting slurry was boiled with stirring and then evaporated to dryness.

The thus evaporated material was crushed. After calcining the crushed material at 200° C for 2 hrs. and subsequently at 400° C for 2 hrs., water was added thereto. The mixture was kneaded and molded into a cylindrical shape of 2 mm × 2 mm$\phi$. After drying at 130° C for 16 hrs., the cylindrical molding was calcined at 850° C for 5 hrs. in air.

The thus obtained catalyst was the catalyst used in Comparison Example 1 below.

The thus obtained catalyst (300 g) was impregnated with a solution which was prepared by dissolving 3.0 g of ammonium tungstate and 7.9 of telluric acid in water and dried, which was followed by calcining at 750° C for 4 hrs.

As a result, the composition of the catalyst had the empirical formula of $W_{0.5}Te_{1.5}Fe_{10}Sb_{60}O_{140}\cdot(SiO_2)_{60}$. The catalyst thus obtained was the catalyst used in Example 1 below.

The catalysts of Example 1 and Comparison Example 1 were tested under Test Condition 1, and the results obtained are shown in Table 1 hereinafter.

Comparison Example 2 and Example 2

A catalyst having the empirical formula of $W_{0.5}Te_2Co_{10}Sb_{25}O_{66}\cdot(SiO_2)_{60}$ was prepared as follows.

To 225 ml of heated nitric acid (specific gravity: 1.38) was gradually added 60.9 g of metal antimony powder (below 100 mesh). After the addition of the antimony powder was completed and the evolution of a brown gas ceased, the mixture was allowed to stand at room temperature for 16 hrs. Thereafter, the excess nitric acid was removed and the precipitate was washed 3 times with 100 ml of water each time (I).

In 200 ml of water was dissolved 58.2 g of cobalt nitrate (II).

Telluric acid (18.4 g) was dissolved in 100 ml of water. In the solution was dissolved 31.4 g of ammonium tungstate (III).

361 g of silica sol ($SiO_2$: 20% by weight) was used as a carrier component (IV).

The components (I) to (IV) were thoroughly mixed, heated with sufficient stirring and then evaporated to dryness.

The evaporated material thus obtained was crushed. After calcining the crushed material at 200° C for 2 hrs. and subsequently at 400° C for 2 hrs., water was added thereto. The mixture was then kneaded and molded into a cylindrical shape of 2 mm × 2 mm$\phi$. After drying at 130° C for 16 hrs., the cylindrical molding was calcined at 800° C for 5 hrs. The thus obtained catalyst was the catalyst used in Comparison Example 2 below.

A catalyst having the empirical formula of $W_{0.5}Te_2Co_{10}Sb_{25}O_{66}\cdot(SiO_2)_{60}$ was prepared as follows. Firstly, a catalyst having the empirical formula of $Co_{10}Sb_{25}O_{20}\cdot(SiO_2)_{60}$ was prepared in accordance with Comparison Example 2 except that the calcination of the catalyst was carried out at 830° C for 5 hrs.

The thus obtained catalyst (300 g) was impregnated with a solution which was prepared by dissolving 4.7 g of ammonium tungstate and 16.6 g of telluric acid in water, and dried, which was followed by calcining at 720° C for 4 hrs. As a result, the composition of the catalyst had an empirical formula of $W_{0.5}Te_2Co_{10}Sb_{2}$- $_5O_{68}\cdot(SiO_2)_{60}$. The catalyst thus obtained was the catalyst used in Example 2 below.

The catalysts of Example 2 and Comparison Example 2 were tested under Test Condition 1, and the results obtained are shown in Table 1 hereinafter.

Comparison Example 3 and Example 3

A catalyst having the empirical formula of $Te_2$- $Ni_{10}Sb_{60}O_{134}\cdot(SiO_2)_{60}$ was prepared in a similar manner to Comparison Example 2 except that nickel nitrate was employed in place of the cobalt nitrate and no ammonium tungstate was added. The calcination of the catalyst was carried out at 750° C for 5 hrs. The catalyst thus obtained was the catalyst used in Comparison Example 3 below.

When the catalyst was tested under Test Condition 1, the results showed a total conversion rate of propylene of 92% and a yield of acrylonitrile of 67%. The reaction was continued for a long period of time, and during that period of time the amount of the air supplied was decreased. As a result, the performance of the reaction was deteriorated. This caused an increase in the formation of carbon dioxide gas. Further, the yield of acrylonitrile decreased to 60%.

The catalyst was impregnated with an aqueous solution which was prepared by dissolving ammonium molybdate and telluric acid in water. After drying, the thus impregnated catalyst was calcined at 720° C for 4 hrs. The composition of the thus impregnated catalyst was $Mo_{0.41}Te_{2.2}Ni_{10}Sb_{60}O_{136}\cdot(SiO_2)_{60}$, which was used as the catalyst of Comparison Example 3. The catalyst was tested under Test Condition 1, and the results are shown in Table 1 hereinafter.

Comparison Example 4 and Example 4

A catalyst having the empirical formula of $Te_1Mn_{10}Sb_{25}O_{72}\cdot(SiO_2)_{30}$ was prepared in a similar manner to Comparison Example 2 except that manganese nitrate was employed in place of the cobalt nitrate and no ammonium tungstate was added. The calcination of the catalyst was carried out at 800° C for 5 hrs. The catalyst thus obtained was used as the catalyst of Comparison Example 4.

Onto this catalyst was sprayed a solution containing ammonium molybdate, telluric acid and zirconium oxynitrate. After drying, the sprayed catalyst was calcined at 200° C for 2 hrs. and subsequently 400° C for 2 hrs. and finally at 700° C for 3 hrs. The composition of the catalyst was $Mo_{0.5}Te_{1.2}Zr_{0.3}Mn_{10}Sb_{25}O_{75}\cdot(SiO_2)_{30}$, which was used as the catalyst of Example 4. The catalysts of Example 4 and Comparison Example 4 were tested under Test Condition 1. The results of which are shown in Table 1 hereinafter.

Comparison Example 5 and Example 5

A catalyst having the empirical formula of $W_{0.1}Te_{0.5}U_{10}Sb_{50}O_{128}\cdot(SiO_2)_{60}$ was prepared in a similar manner to Comparison Example 2 except that uranyl nitrate was employed in place of the cobalt nitrate. The calcination of the catalyst as carried out at 900° C for 2 hrs., and was used as the catalyst of Comparison Example 5.

The catalyst thus obtained was impregnated with a solution which was prepared by dissolving ammonium molybdate, telluric acid and potassium nitrate in water. Thereafter, the catalyst thus impregnated was dried and then was calcined at 720° C for 4 hrs. The composition of the thus impregnated catalyst had the empirical formula of $Mo_{0.25}W_{0.1}Te_{1.0}K_{0.2}U_{10}Sb_{50}O_{130}\cdot(SiO_2)_{60}$.

The catalysts of Example 5 and Comparison Example 5 were tested under Test Condition 1, and the results obtained are shown in Table 1 hereinafter.

Comparison Example 6 and Example 6

A catalyst having the empirical formula of $Sn_{10}Sb_{60}O_{140}\cdot(SiO_2)_{60}$ was prepared in a similar manner to Comparison Example 1 except that metallic tin powder was employed in place of the electrolytic iron powder. The calcination of the catalyst was carried out at 850° C for 5 hrs., and the catalyst was used as the catalyst in Comparison Example 5.

Onto the thus obtained catalyst was sprayed a solution which was prepared by dissolving ammonium vanadate and telluric acid in water. Thereafter, the catalyst thus sprayed was dried and then calcined at 700° C for 5 hrs. The composition of the thus prepared catalyst had the empirical formula of $V_{0.1}Te_{1.0}Sn_{10}Sb_{60}O_{142}\cdot(SiO_2)_{60}$, and was used as the catalyst of Example 6. The catalysts of Comparison Example 6 and Example 6 were tested under Test Condition 1, and the results obtained are shown in Table 1 hereinafter.

Comparison Example 7 and Example 7

A catalyst having the empirical formula of $W_{0.5}Te_{1.0}Cu_{3.0}Fe_{10}Sb_{25}O_{72}\cdot(SiO_2)_{30}$ was prepared in a similar manner to Comparison Example 1 except that ammonium tungstate, tellurium dioxide and copper nitrate were further incorporated in the system prior to adjusting the pH. The calcination of the catalyst was carried out at 810° C for 3 hrs. Using this catalyst, ammoxidation of propylene was carried out under Test Condition 1. Acrylonitrile was obtained in the yield of 77% at a reaction temperature of 460° C. Then, the reaction temperature was increased to 490° C. The reaction was continued such that the partial pressure of oxygen around the outlet of the reactor was almost zero.

The reaction temperature was again reduced to 460° C. However, the formation of carbon dioxide gas was increased and the yield of acrylonitrile was decreased.

Onto this catalyst was sprayed an aqueous solution of ammonium tungstate, telluric acid, zinc nitrate and magnesium nitrate. Thereafter, the catalyst thus sprayed was dried and then calcined at 720° C for 5 hrs. The composition of the thus prepared catalyst had the empirical formula $W_{0.75}Te_{1.5}Zn_{0.2}Mg_{0.1}Cu_{3.0}Fe_{10}Sb_{25}O_{74}\cdot(SiO_2)_{30}$, and was used as the catalyst of Example 7.

The catalysts of Example 7 Comparison Example 7 were tested under Test Condition 1, 1 and the results obtained are shown in Table 1 hereinafter.

Comparison Example 8-1 and Example 8-1

A catalyst having the empirical formula of $W_{0.25}Te_{1.0}Fe_{10}Sb_{25}O_{68}\cdot(SiO_2)_{30}$ was prepared as follows.

Metallic antimony powder (1.95 kg) having a particle size of below 100 microns was gradually added to 7.2 liters of nitric acid (specific gravity: 1.38) which was previously heated to about 80° C. After the antimony was confirmed to be completely oxidized, the excess nitric acid was removed. Then, the antimony oxidized with nitric acid was washed five times with 2 liters of water. The oxide was transferred to a ball mill and ground for 3 hrs.(I).

Electrolytic iron powder (0.358 kg) was employed. Nitric acid (3 liters)(specific gravity: 1.38)was mixed with 4 liters of water and the mixture was heated to about 80° C. The iron powder was gradually added to the heated mixture to completely dissolve the iron powder (II).

Ammonium tungstate (41.8 g) was dissolved in 2 liters of water (III).

Telluric acid (147 g) was dissolved in 1 liter of water (IV).

Silica sol (3.84 g) : (tradename LUDOX HS: containing 30% by weight of $SiO_2$ produced by Du Pont) was used (V).

Components (I) to (V) described above were mixed. To the mixture was gradually added aqueous ammonia (concentration: 15% by weight) with sufficiently stirring to adjust the pH to 2. The resulting slurry thus obtained was heated with thorough stirring. The heating was continued at 100° C for 4 hrs. The slurry was then spray dried and the thus obtained finely divided spherical particles were calcined at 200° C for 2 hrs., at 400° C for 4 hrs. and at 800° C for 8 hrs., subsequently. The catalyst thus prepared was used as the catalyst of Comparison Example 8-1.

To the catalyst (5 kg) was added an impregnating liquid prepared by dissolving 8.7 g of ammonium metavanadate and 86.1 g of telluric acid in water to make the total amount 1.6 liter. The mixture was mixed for 1 hr., and dried at 120° C for 16 hrs., followed by calcination at 400° C for 4 hrs. and at 720° C for 4 hrs. Thus, the composition of the catalyst had the empirical formula of $V_{0.1}W_{0.25}Te_{1.5}Fe_{10}Sb_{25}O_{69}\cdot(SiO_2)_{30}$. The catalyst thus prepared was used as the catalyst of Example 8-1. the catalysts of Example 8-1 and Comparison Example 8-1 were tested under Test Condition 2, and the results obtained are shown in Table 1 hereinafter.

EXAMPLE 8-2

A catalyst having the empirical formula of $V_{0.1}Ni_{0.2}W_{0.25}Te_{1.5}Fe_{10}Sb_{25}O_{69}\cdot(SiO_2)_{30}$ was prepared as follows.

The catalyst of Comparison Example 8-1 (5 kg) was employed and an impregnating liquid prepared by dissolving 8.7 g of ammonium metavanadate, 86.1 g of telluric acid and 50 g of nickel nitrate in water to make the total amount 1.6 liters was added thereto. The mixture was mixed for 1 hr. and dried at 120° C for 16 hrs., followed by calcination at 400° C for 4 hrs. and at 720° C for 4 hrs. The catalyst thus prepared was tested under Test Condition 2, and the results obtained are shown in Table 1 hereafter.

EXAMPLE 8-3

A catalyst having the empirical formula of $Mo_{0.2}W_{0.25}Te_{1.5}Fe_{10}Sb_{25}O_{69}\cdot(SiO_2)_{30}$ was prepared in a similar manner to Example 8-1 except that ammonium molybdate was employed instead of ammonium metavanadate. The final calcination of the catalyst was carried out at 720° C for 4 hrs. The catalyst thus prepared was tested under Test Condition 2, and the results obtained are shown in Table 1 hereafter.

EXAMPLE 8-4

A catalyst having the empirical formula of $Mo_{0.2}W_{0.25}Te_{1.5}Cu_{0.2}Fe_{10}Sb_{25}O_{70}\cdot(SiO_2)_{30}$ was prepared in a similar manner to Example 8-2 except that ammonium molybdate and copper nitrate were employed instead of ammonium metavanadate and nickel nitrate, respectively. The final calcination of the catalyst was carried out at 720° C for 4 hrs. The catalyst thus prepared was tested under Test Condition 2, and the results obtained are shown in Table 1 hereafter.

Comparison Example 8-2

A catalyst having the empirical formula of $Mo_{0.2}W_{0.25}Te_{10}Fe_{10}Sb_{25}O_{68}\cdot(SiO_2)_{30}$ was prepared in a similar manner to Example 8-1 except that the impregnating liquid employed contained ammonium molybdate instead of ammonium metavanadate and contained no telluric acid, i.e., contained only a molybdenum component. The final calcination of the catalyst was carried out at 720° C for 4 hrs. The catalyst thus prepared was tested under Test Condition 2, and the results obtained are shown in Table 1 hereinafter.

Comparison Example 8-3

A catalyst having the empirical formula of $Mo_{1.0}Te_{1.5}Ni_5Fe_{12}Sb_{25}O_{79}\cdot(SiO_2)_{60}$ was prepared in a similar manner to Comparison Example 1 except that ammonium molybdate, telluric acid and nickel nitrate were additionally incorporated into the catalyst.

After molding and drying, the catalyst was divided into four groups, which were calcined for 4 hrs. at 800° C, 810° C, 820° C and 830+ C, respectively.

The test results of the catalyst calcined at 810° C are shown in Table 1 hereafter. Further, the relationship between the calcination temperature and the specific surface area is shown in FIG. 1. The relationship between the calcination temperature and the yield of acrylonitrile is shown in FIG. 2.

EXAMPLE 8-5

A catalyst having the same composition as in Comparison Example 8-3, i.e., $Mo_{1.0}Te_{1.5}Ni_5Fe_{12}Sb_{25}O_{79}\cdot(SiO_2)_{60}$, was prepared as follows.

First, a catalyst having the empirical formula of $Mo_{0.7}Te_{1.0}Ni_5Fe_{12}Sb_{25}O_{77}\cdot(SiO_2)_{60}$ was prepared in a similar manner to Comparison Example 8-3. The final calcination was carried out at 790° C for 5 hrs.

Then, the catalyst was impregnated for 2 hrs. with an aqueous solution containing ammonium molybdate and telluric acid. By measuring the pore volume the concentration of the impregnating liquid was determined so that the final composition was $Mo_{1.0}Te_{1.5}Ni_5Fe_{12}Sb_{25}O_{79}\cdot(SiO_2)_{60}$.

The catalyst was removed from the impregnating liquid and dried at 130° C for 16 hrs., followed by calcination at 200° C for 2 hrs. and at 400° C for 2 hrs. The thus calcined catalyst was divided into four groups, each of which was calcined for 4 hrs. at 690° C, 700° C, 710° C and 720° C, respectively.

The results obtained with the catalyst calcined at 710° C are shown in Table 1 hereinafter. The relationship between the calcination temperature and specific surface area is shown in FIG. 3. The relationship between the calcination temperature and the yield of acrylonitrile is shown in FIG. 4.

Table 1

Test for Activity of Catalyst [Ammoxidation of Propylene]

| Ex. No. | Composition of Catalyst (Atomic Ratio) | Test Condition | Reaction Temperature (° C) | Total Conversion Rate of Propylene (%) | Yield of Acrylonitrile (%) | Selectivity of Acrylonitrile (%) |
|---|---|---|---|---|---|---|
| Ex. 1 | $W_{0.5}Te_{1.5}Fe_{10}Sb_{60}Si_{60}$ | 1 | 440 | 97 | 73 | 75 |
| Comparison Ex. 1 | $Fe_{10}Sb_{60}Si_{60}$ | 1 | 450 | 96 | 68 | 71 |
| Ex. 2 | $W_{0.5}Te_2Co_{10}Sb_{25}Si_{60}$ | 1 | 450 | 97 | 72 | 74 |
| Comparison Ex. 2 | $W_{0.5}Te_2Co_{10}Sb_{25}Si_{60}$ | 1 | 450 | 95 | 68 | 72 |
| Ex. 3 | $Mo_{0.4}Te_{2.2}Ni_{10}Sb_{60}Si_{60}$ | 1 | 450 | 93 | 71 | 76 |
| Comparison Ex. 3 | $Te_2Ni_{10}Sb_{60}Si_{60}$ | 1 | 460 | 90 | 60 | 67 |
| Ex. 4 | $Mo_{0.5}Te_{1.2}Zr_{0.3}Mn_{10}Sb_{25}Si_{30}$ | 1 | 450 | 98 | 72 | 74 |
| Comparison Ex. 4 | $Te_{1.0}Mn_{10}Sb_{25}Si_{30}$ | 1 | 450 | 92 | 68 | 74 |
| Ex. 5 | $Mo_{0.25}W_{0.1}Te_{1.0}K_{0.2}U_{10}Sb_{50}Si_{60}$ | 1 | 470 | 96 | 76 | 79 |
| Comparison Ex. 5 | $W_{0.1}Te_{0.5}U_{10}Sb_{50}Si_{60}$ | 1 | 480 | 94 | 73 | 78 |
| Ex. 6 | $V_{0.1}Te_{1.0}Sn_{10}Sb_{60}Si_{60}$ | 1 | 450 | 95 | 72 | 76 |
| Comparison Ex. 6 | $Sn_{10}Sb_{60}Si_{60}$ | 1 | 460 | 93 | 63 | 68 |
| Ex. 7 | $W_{0.75}Te_{1.5}Zn_{0.2}Mg_{0.1}Cu_3Fe_{10}Sb_{25}Si_{30}$ | 1 | 450 | 98 | 79 | 81 |
| Comparison Ex. 7 | $W_{0.5}Te_{1.0}Cu_3Fe_{10}Sb_{25}Si_{30}$ | 1 | 460 | 96 | 71 | 74 |
| Ex. 8-1 | $V_{0.1}W_{0.25}Te_{1.5}Fe_{10}Sb_{25}Si_{30}$ | 2 | 460 | 97 | 81 | 84 |
| Comparison Ex. 8-1 | $W_{0.25}Te_{1.0}Fe_{10}Sb_{25}Si_{30}$ | 2 | 470 | 98 | 80 | 82 |
| Ex. 8-2 | $V_{0.1}Ni_{0.2}W_{0.25}Te_{1.5}Fe_{10}Sb_{25}Si_{30}$ | 2 | 460 | 98 | 82 | 83 |
| Ex. 8-3 | $Mo_{0.2}W_{0.25}Te_{1.5}Fe_{10}Sb_{25}Si_{30}$ | 2 | 430 | 96 | 81 | 83 |
| Ex. 8-4 | $Mo_{0.2}W_{0.5}Te_{1.5}Cu_{0.2}Fe_{10}Sb_{25}Si_{30}$ | 2 | 430 | 98 | 83 | 85 |
| Comparison Ex. 8-2 | $Mo_{0.2}W_{0.25}Te_{1.0}Fe_{10}Sb_{25}Si_{30}$ | 2 | 430 | 97 | 77 | 79 |
| Comparison Ex. 8-3 | $Mo_{1.0}Te_{1.5}Ni_5Fe_{12}Sb_{25}Si_{60}$ | 2 | 430 | 98 | 77 | 79 |
| Ex. 8-5 | $Mo_{1.0}Te_{1.5}Ni_5Fe_{12}Sb_{25}Si_{60}$ | 2 | 430 | 97 | 79 | 81 |

Comparison Example 9 and Example 9

A catalyst having the empirical formula of $Mo_{10}Te_1Fe_{10}Sb_{50}O_{147}\cdot(SiO_2)_{30}$ was prepared in a similar manner to Comparison Example 1 except that ammonium molybdate and telluric acid were further incorporated into the catalyst. The final calcination of the catalyst was carried out at 650° C for 4hrs. The thus prepared catalyst was used as the catalyst of Comparison Example 9.

Onto the catalyst was sprayed a solution which was prepared by dissolving ammonium metavanadate, ammonium molybdate, telluric acid and aluminum nitrate in water. After drying, the catalyst was calcined at 650° C for 4 hrs. The composition of the thus prepared catalyst had the empirical formula of $Mo_{10.2}V_{0.1}Te_2Al_{0.5}Fe_{10}Sb_{50}O_{151}\cdot(SiO_2)_{30}$, and was used as the catalyst of Example 9. The catalysts of Example 9 and Comparison Example 9 were tested under Test Condition 3, and the results obtained are shown in Table 2 hereafter.

Comparison Example 10 and Example 10

A catalyst having the empirical formula of $W_{0.5}Te_{1.0}Ni_5Fe_{10}Sb_{25}O_{74}\cdot(SiO_2)_{30}$ was prepared in a similar manner to Comparison Example 1 except that ammonium tungstate, the oxide obtained by oxidation of metallic tellurium powder with nitric acid and nickel nitrate were further incorporated into the catalyst. The final calcination of the catalyst was carried out at 810° C. for 4hrs. The catalyst thus prepared was used as the catalyst o Comparison Example 10.

Onto the catalyst was sprayed a solution which was prepared by dissolving ammonium metavanadate, telluric acid, manganese nitrate and copper nitrate in water. After drying, the catalyst was calcined at 700° C for 5 hrs. The empirical formula of the catalyst thus prepared was $V_{0.1}W_{0.5}Te_{1.5}Mn_{0.1}Cu_{0.1}Ni_5Fe_{10}Sb_{25}O_{75}.(SiO_2)_{30}$, and the catalyst was used as the catalyst of Example 10.

The catalysts of Example 10 and Comparison Example 10 were tested under Test Condition 3 and Test Condition 4, respectively, and the results obtained are shown in Table 2 and Table 3 hereinafter.

Table 2

Test for Activity of Catalyst [Ammoxidation of Isobutylene]

| Example No. | Composition of Catalyst (Atomic Ratio) | Test-Condition | Reaction Temperature (° C) | Total-Conversion Rate of Isobutene (%) | Yield of Methacylonitrile (%) | Selectivity of Methacylonitrile (%) |
|---|---|---|---|---|---|---|
| Example 9 | $Mo_{10.2}V_{0.1}Te_2Al_{0.5}Fe_{10}Sb_{50}Si_{30}$ | 3 | 420 | 93 | 68 | 73 |
| Comparison Example 9 | $Mo_{10}Te_1Fe_{10}Sb_{50}Si_{30}$ | 3 | 430 | 94 | 65 | 69 |
| Example 10 | $V_{0.1}W_{0.5}Te_{1.5}Mn_{0.1}Cu_{0.1}Ni_5Fe_{10}Sb_{25}Si_{30}$ | 3 | 410 | 95 | 65 | 69 |
| Comparison Example 10 | $W_{0.5}Te_{1.0}Ni_5Fe_{10}Sb_{25}Si_{30}$ | 3 | 410 | 97 | 60 | 62 |

Table 3

Test for Activity of Catalyst [Oxidative Dehydrogenation of Butene-1]

| Example No. | Composition of Catalyst (Atomic Ratio) | Test Condition | Reaction Temperature (° C) | Total Conversion Rate of Butene-1 (%) | Yield of Butadiene (%) | Selectivity of Butadiene (%) |
|---|---|---|---|---|---|---|
| Example 10 | $V_{0.1}W_{0.5}Te_{1.5}Mn_{0.1}Cu_{0.1}Ni_5Fe_{10}Sb_{25}Si_{30}$ | 4 | 420 | 98 | 77 | 79 |
| Comparison Example 10 | $W_{0.5}Te_{1.0}Ni_5Fe_{10}Sb_{25}Si_{30}$ | 4 | 410 | 97 | 75 | 77 |

Comparison Example 11 and Example 11

A catalyst having the empirical formula of $V_{0.25}Te_{1.0}Cu_{10}Sb_{25}O_{63}.(SiO_2)_{30}$ was prepared in a similar manner to Comparison Example 2 except that copper nitrate and ammonium metavanadate were employed instead of cobalt nitrate and ammonium tungstate, respectively. The final calcination of the catalyst was carried out at 800° C for 5hrs., and the catalyst was used in Comparison Example 11.

Onto the catalyst was sprayed a solution which was prepared by dissolving ammonium molybdate, telluric acid and bismuth nitrate in nitric acid. After drying, the catalyst was calcined at 700° C for 5hrs. The empirical formula of the catalyst thus prepared was $Mo_{0.2}V_{0.25}Bi_{0.2}Te_{3.6}Cu_{10}Sb_{25}O_{129}.(SiO_2)_{30}$. The catalyst thus obtained was used as the catalyst of Example 11.

The catalysts of Example 11 and Comparison Example 11 were tested under Test Condition 4, and the results obtained are shown in Table 4 hereinbelow.

Comparison Example 12 and Example 12

A catalyst having the empirical formula of $V_{0.1}Te_{2.0}Co_5Fe_{10}Sb_{50}O_{124}.(SiO_2)_{60}$ was prepared in a similar manner to Comparison Example 1 except that ammonium metavanadate, telluric acid and cobalt nitrate were further incorporated into the catalyst. The final calcination of the catalyst was carried out at 800° C for 5 hrs. The catalyst thus prepared was used as the catalyst Comparison Example 12.

Onto the catalyst was sprayed a solution which was prepared by dissolving ammonium molybdate, ammonium tungstate, cobalt nitrate, nickel nitrate and telluric acid in water. After drying, the catalyst was calcined at 670° C for 5 hrs. The composition of the catalyst thus prepared had the emperical formula of $V_{0.1}Mo_{0.1}W_{0.1}Te_{2.2}Ni_{0.2}Co_{5.1}Fe_{10}Sb_{50}O_{121}.(SiO_2)_{60}$, and was used as the catalyst of Example 12.

The catalysts of Example 12 and Comparison Example 12 were tested under Test Condition 5, and results obtained are shown in Table 4 hereinbelow.

Table 4

Test for Activity of Catalyst (Oxidation of Propylene)

| Example No. | Composition of Catalyst (Atomic Ratio) | Test Condition | Reaction Temp. (° C) | Total Conversion Rate of Propylene (%) | Yield of Acrolein (%) | Selectivity of Acrolein (%) |
|---|---|---|---|---|---|---|
| Example 11 | $Mo_{0.2}V_{0.25}Bi_{0.2}Te_{3.6}Cu_{10}Sb_{25}Si_{30}$ | 5 | 410 | 78 | 52 | 67 |
| Comparison Example 11 | $V_{0.25}Te_{1.0}Cu_{10}Sb_{25}Si_{30}$ | 5 | 420 | ~63 | 35 | 56 |
| Example 12 | $V_{0.1}Mo_{0.1}W_{0.1}Te_{2.2}Ni_{0.2}Co_{5.1}Fe_{10}Sb_{50}Si_{60}$ | 5 | 430 | 86 | 60 | 70 |
| Comparison Example 12 | $V_{0.1}Te_{2.0}Co_5Fe_{10}Sb_{50}Si_{60}$ | 5 | 430 | 83 | 53 | 64 |

While the invention has been described in detail and with reference to specific embodiments thereof, it will be apparent to one skilled in the art that various changes and modifications can be made therein without departing from the spirit and scope thereof.

What is claimed is:

1. A process for producing a catalyst comprising an antimony-containing oxide which comprises the steps of (A) calcining a mixture of metal oxides containing, as essential components, an oxide of antimony and an oxide of at least one metal selected from the group consisting of iron, cobalt, nickel, manganese, uranium, tin and copper, said calcining being at temperatures of from about 500° C to about 1000° C; (B) impregnating with or spraying onto said calcined mixture of metal oxides (a) an aqueous solution or a suspension containing (1) at least one compound of a metal selected from the group consisting of molybdenum, vanadium and tungsten, said metal compound being thermally convextible to an oxide of said metal, and (2) a tellurium compound, said tellurium compound being thermally convertible to a tellurium oxide, or (b) an aqueous solution or a suspension containing said metal compound (1)

and an aqueous solution or a suspension containing said tellurium compound (2); (C) drying said impregnated or sprayed mixture of metal oxides; and (D) calcining said dried mixture of metal oxides at a temperature of from about 400° C to about 850° C, where said calcining (D) is at a temperature lower than said calcining (A).

2. The process according to claim 1, wherein at least one of said aqueous solution or suspension containig said at least one compound of a metal selected from the group consisting of molybdenum, vanadium and tungsten and said tellurium compound, said aqueous solution or suspension containing said at least one compound of a metal selected from the group consisting of molybdenum, vanadium and tungsten, and said aqueous solution or suspension of said tellurium compound additionally contains at least one compound of an additional metal selected from the group consisting of iron, cobalt, nickel, manganese, copper, zinc, potassium, magnesium, aluminum, zirconium, bismuth, lanthanum, cerium, chromium, phosphorus and boron, said additional metal compound being thermally convertible to an oxide of said additional metal.

3. The process according to claim 1, wherein the catalyst produced is represented by the empirical formula:

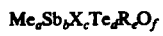

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represents the atomic ratio of the component with which the subscript is associated in which:
  when a is 10,
  b = about 5-60
  c = about 0.05-30
  d = about 0.05-10
  e = about 0-20, and
  f = the number of oxygens corresponding to the oxides formed by each of the components described above.

4. The process according to claim 2, wherein the catalyst produced is represented by the empirical formula:

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represents the atomic ratio of the component with which the subscript is associated in which:
  when a is 10,
  b = about 5-60.
  c = about 0.05-30
  d = about 0.05-10
  e = about 0-20, and
  f = the number of oxygens corresponding to the oxides formed by each of the corresponding described above.

5. The process according to claim 3, wherein the catalyst produced is represented by the empirical formula:

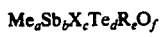

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represent the atomic ratio of the component with which the subscript is associated in which:
  when a is 10,
  b = 5-60
  c = 0.1-15
  d = 0.1-5
  e = 0-10, and
  f = the number of oxygens corresponding to the oxides formed by each of the corresponding described above.

6. The process according to claim 4, wherein the catalyst produced is represented by the empirical formula:

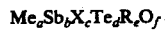

$Me_aSb_bX_cTe_dR_eO_f$ wherein Me is at least one componenet selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscribers a, b, c, d, e and f each represent the atomic ratio of the component with which the subscriber is associated in which:
  when a is 10,
  b = 5-60
  c = 0.1-15
  d = 0.1-5
  e = 0-10, and
  f = the number of oxygens corresponding to the oxides formed by each of the components described above.

7. The process according to claim 1, wherein said mixture of metal oxides is carried on an inert carrier.

8. The process according to claim 2, wherein mixture of metal oxides is carried out on an inert carrier.

9. The process according to claim 7, wherein said inert carrier is silica.

10. The process according to claim 8, wherein said inert carrier is silica.

11. A process for reactivating a catalyst comprising a metal oxide mixture containing, as essential components, an oxide of antimony and an oxide of at least one metal selected from the group consisting or iron, cobalt, nickel, manganese, uranium, tin and copper, and further containing, as additive components, (1) an oxide of at least one metal selected from the group consisting of molybdenum, vanadium, and tungsten and (2) an oxide of tellurium, which comprises impregnating with or spraying onto said catalyst having reduced catalytic activity, (a) an aqueous solution or a suspension containing (1) at least one compound of a metal selected from the group consisting of molybdenum, vanadium and tungsten, said metal compound being thermally convertible to an oxide of said metal, and (2) a tellurium compound, said tellurium compound being thermally convertible to a tellurium oxide, or (b) an aqueous solution or a suspension containing said metal compound (1) and an aqueous solution or a suspension containing said tellurium compound (2); drying the thus-obtained catalyst; and calcining the thus-obtained catalyst at a temperature of from about 440° C to about 850° C.

12. The process according to claim 11, wherein at least one of said aqueous solution or suspension containing said at least one compound of a metal selected from the group consisting of molybdenum, vanadium and tungsten and said tellurium compound, said aqueous solution or suspension containing said at least one compound of a metal selected from the group consisting of molybdenum, vanadium and tungsten, and said aqueous solution or suspension containing said tellurium compound additionally contains at least one compound of an additional metal selected from the group consisting of iron, cobalt, nickel, manganese, copper, zinc, potassium, magnesium, aluminum, zirconium, bismuth, lanthanum, cerium, chronium, phosphorus and boron, said additional metal compound being thermally convertible to an oxide of said additional metal.

13. The process according to claim 11, wherein the catalyst produced is represented by the empirical formula:

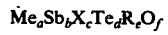

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represents the atomic ratio of the component with which the subscript is associated in which:
when n is 10,
b = about 5–60
c = about 0.05–30
d = about 0.05–10
e = about 0–20, and
f = the number of oxygens corresponding to the oxides formed by each of the components described above.

14. The process according to claim 12, wherein the catalyst produced is represented by the empirical formula:

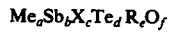

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represents the atomic ratio of the component with which the subscript is associated with:
when a is 10,
b = about 5–60
c = about 0.05–30
d = about 0.05–10
e = about 0–20, and f = the number of oxygens corresponding to the oxides formed by each of the components described above.

15. The process according to claim 13, wherein the catalyst produced is represented by the empirical formula:

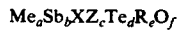

$Me_aSb_bXZ_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, Mg, Al, Zr, Bi, La, Ce, Cr, P and B; and the subscripts a, b, c, d, e and f each represnts the atomic ratio of the component with which the subscript is associated in which:
when a is 10,
b = 5–60
c = 0.1–15
d = 0.1–5
e = 0–10, and
f = the number of oxygen corresponding to the oxides formed by each of the components described above.

16. The process according to claim 14, wherein the catalyst produced is represented by the empirical formual:

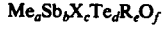

$Me_aSb_bX_cTe_dR_eO_f$ wherein Me is at least one component selected from the group consisting of Fe, Co, Ni, Mn, U, Sn and Cu; X is at least one component selected from the group consisting of Mo, V and W; R is at least one component selected from the group consisting of Zn, K, MG, Al, Zr, Be, La, Ce, Cr, P and B; and the subscripts a, b, c, d, e, and f each represents the atomic ratio of the component with which the subscript is associated in which:
when a is 10,
b = 5–60
c = 0.1–15
d = 0.1–5
e = 0–10, and
f = the number of oxygens corresponding to the oxides formed by each of the components described above.

17. The process according to claim 11, wherein said catalyst is carried on an inert carrier.

18. The process according to claim 12, wherein said catalyst is carried on an inert carrier.

19. The process according to claim 17, wherein said inert carrier is silica.

20. The process according to claim 18, wherein said inert carrier is silica.

21. The process according to claim 1, wherein said impregnating with or spraying onto of said mixture of metal oxides is with said aqueous solution or suspension containing said at least one compound of a metal selected from the group consisting of molybdenum, vanadium and tungsten and said tellurium compound.

22. The process according to claim 11, wherein said impregnating with or spraying onto of said mixture of metal oxides is with said aqueous solution or suspension containing said at least one compound of a metal selected from the group consisting of molybdenum, vanadium and tungsten and said tellurium compound.

* * * * *

UNITED STATES PATENT AND TRADEMARK OFFICE
CERTIFICATE OF CORRECTION

PATENT NO. : 4,049,575

DATED : September 20, 1977

INVENTOR(S) : YUTAKA SASAKI ET AL

It is certified that error appears in the above—identified patent and that said Letters Patent is hereby corrected as shown below:

Claim 11, at Column 23, line 6, delete "440°C" and insert therefor

-- 400°C --.

*Signed and Sealed this*

*Ninth Day of March 1982*

[SEAL]

Attest:

GERALD J. MOSSINGHOFF

*Attesting Officer*     *Commissioner of Patents and Trademarks*